(12) United States Patent
Ozao

(10) Patent No.: US 10,809,523 B2
(45) Date of Patent: Oct. 20, 2020

(54) ENDOSCOPE OBJECTIVE OPTICAL SYSTEM

(71) Applicant: OLYMPUS CORPORATION, Hachioji-shi, Tokyo (JP)

(72) Inventor: Akihiko Ozao, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 284 days.

(21) Appl. No.: 15/955,227

(22) Filed: Apr. 17, 2018

(65) Prior Publication Data

US 2018/0231763 A1 Aug. 16, 2018

Related U.S. Application Data

(63) Continuation of application No. PCT/JP2016/080773, filed on Oct. 18, 2016.

(30) Foreign Application Priority Data

Nov. 26, 2015 (JP) .................. 2015-230522

(51) Int. Cl.
*G02B 21/02* (2006.01)
*G02B 23/24* (2006.01)
(Continued)

(52) U.S. Cl.
CPC ...... *G02B 23/2492* (2013.01); *A61B 1/00096* (2013.01); *A61B 1/00186* (2013.01); *A61B 1/00188* (2013.01); *A61B 1/05* (2013.01); *A61B 1/051* (2013.01); *G02B 5/208* (2013.01); *G02B 9/10* (2013.01); *G02B 23/243* (2013.01); *G02B 7/028* (2013.01); *G02B 13/04* (2013.01)

(58) Field of Classification Search
CPC .. G02B 21/00; G02B 23/2407; G02B 23/243; G02B 23/2492; G02B 5/00; G02B 5/208; G02B 13/04; G02B 13/18; G02B 9/00; G02B 9/10; A61B 1/00096; A61B 1/00186; A61B 1/00188; A61B 1/05; A61B 1/051
See application file for complete search history.

(56) References Cited

U.S. PATENT DOCUMENTS 6,252,723 B1 * 6/2001 Nagaoka ............. G02B 15/173
359/652
7,280,283 B1 * 10/2007 Kasai ................. A61B 1/00179
359/656
(Continued)

FOREIGN PATENT DOCUMENTS

JP 02069710 A 3/1990
JP 09325285 A 12/1997
(Continued)

OTHER PUBLICATIONS

International Search Report (ISR) dated Jan. 24, 2017 issued in International Application No. PCT/JP2016/080773.
(Continued)

*Primary Examiner* — Thong Q Nguyen
(74) *Attorney, Agent, or Firm* — Holtz, Holtz & Volek PC

(57) ABSTRACT

An endoscope objective optical system that is to be combined with a solid image pickup element includes, in order from an object side, a planoconcave negative lens, an absorption-type filter, an aperture stop, and a planoconvex positive lens.

3 Claims, 12 Drawing Sheets

(51) Int. Cl.
*A61B 1/05* (2006.01)
*A61B 1/00* (2006.01)
*G02B 5/20* (2006.01)
*G02B 9/10* (2006.01)
G02B 13/04 (2006.01)
G02B 7/02 (2006.01)

(56) References Cited

U.S. PATENT DOCUMENTS

| | | | |
|---|---|---|---|
| 8,582,218 B2* | 11/2013 | Takasugi | A61B 1/00177 |
| | | | 359/754 |
| 2002/0055669 A1* | 5/2002 | Konno | A61B 1/05 |
| | | | 600/167 |
| 2008/0252997 A1 | 10/2008 | Duckett | |
| 2009/0296235 A1 | 12/2009 | Igarashi | |
| 2009/0303618 A1 | 12/2009 | Machida | |
| 2011/0069400 A1 | 3/2011 | Duckett | |

FOREIGN PATENT DOCUMENTS

| | | |
|---|---|---|
| JP | 2001059937 A | 3/2001 |
| JP | 2008262193 A | 10/2008 |
| JP | 2009288682 A | 12/2009 |
| JP | 2009294494 A | 12/2009 |

OTHER PUBLICATIONS

International Preliminary Report on Patentability (IPRP) (and English language translation thereof) dated Jun. 7, 2018 issued in counterpart International Application No. PCT/JP2016/080773.

\* cited by examiner

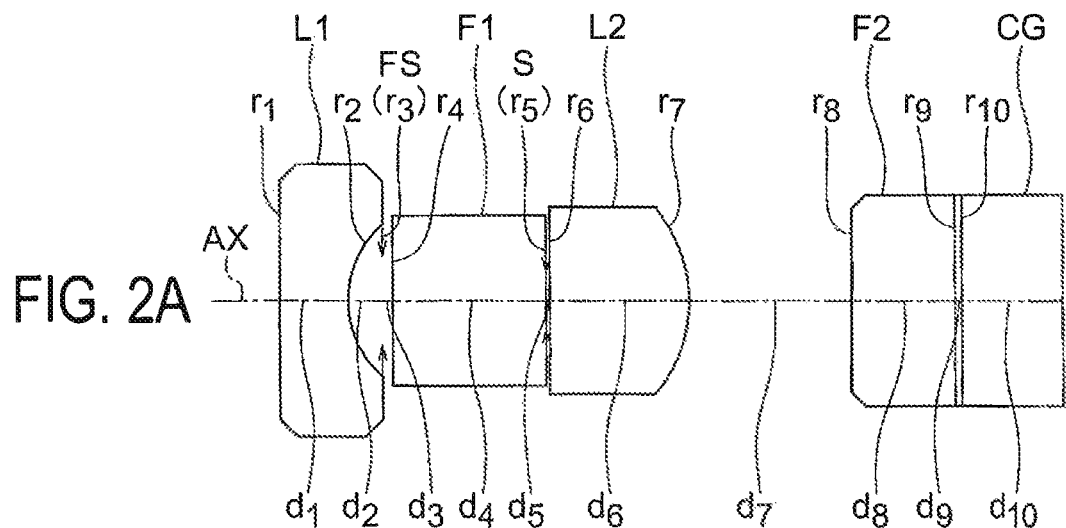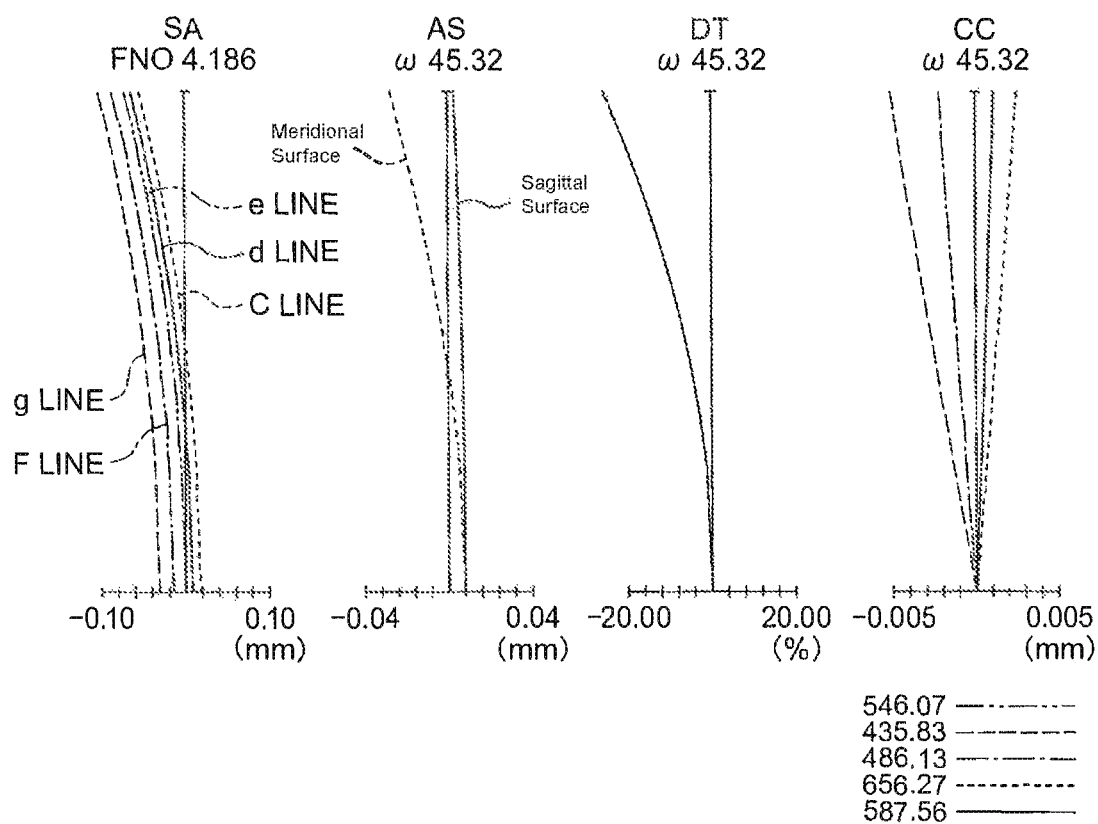

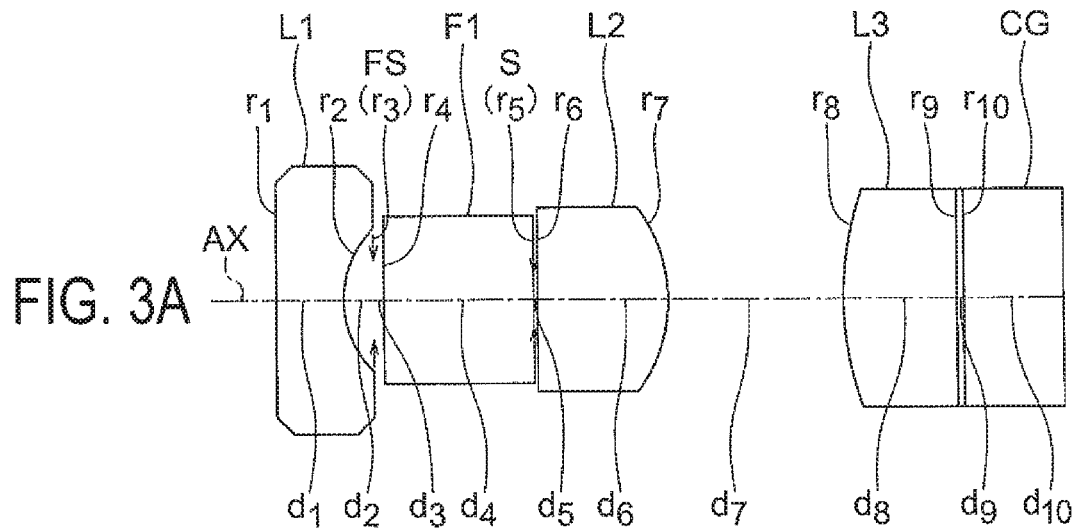
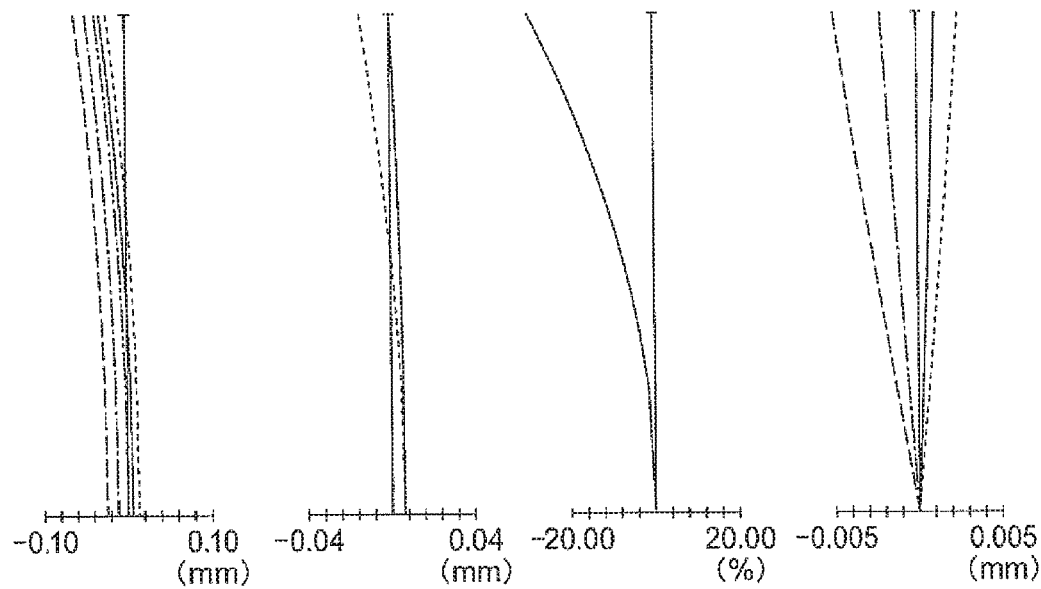

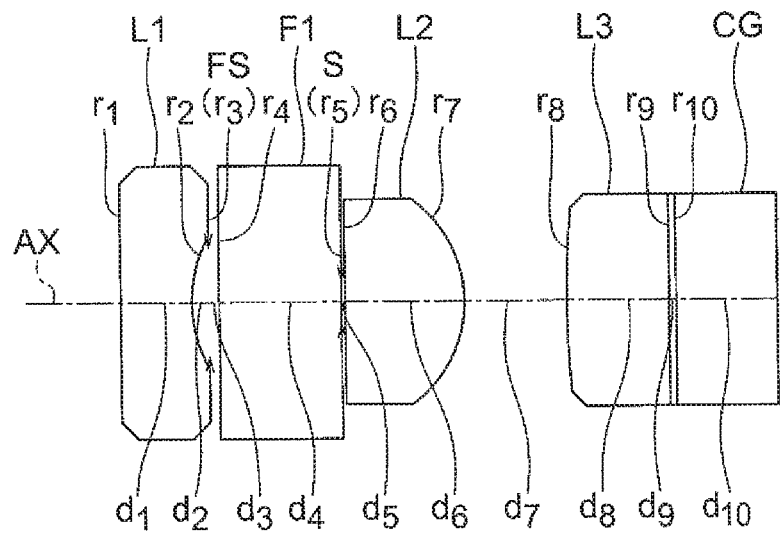
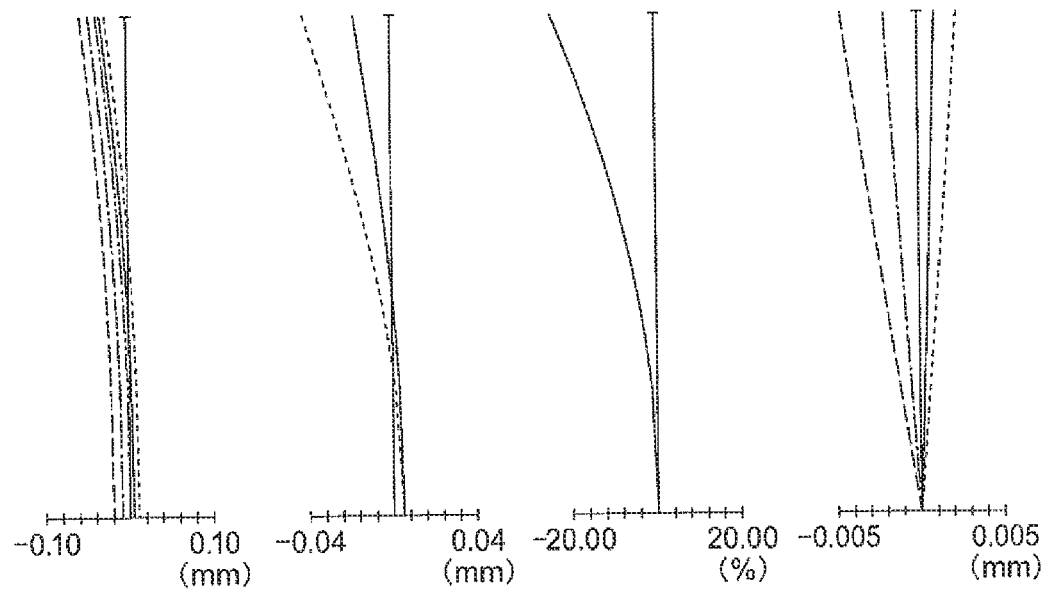

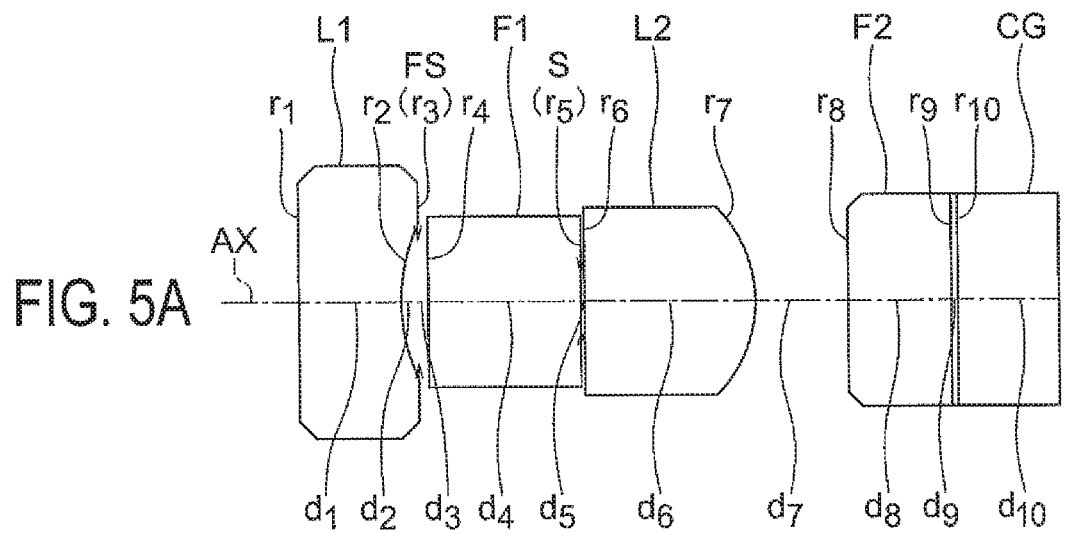
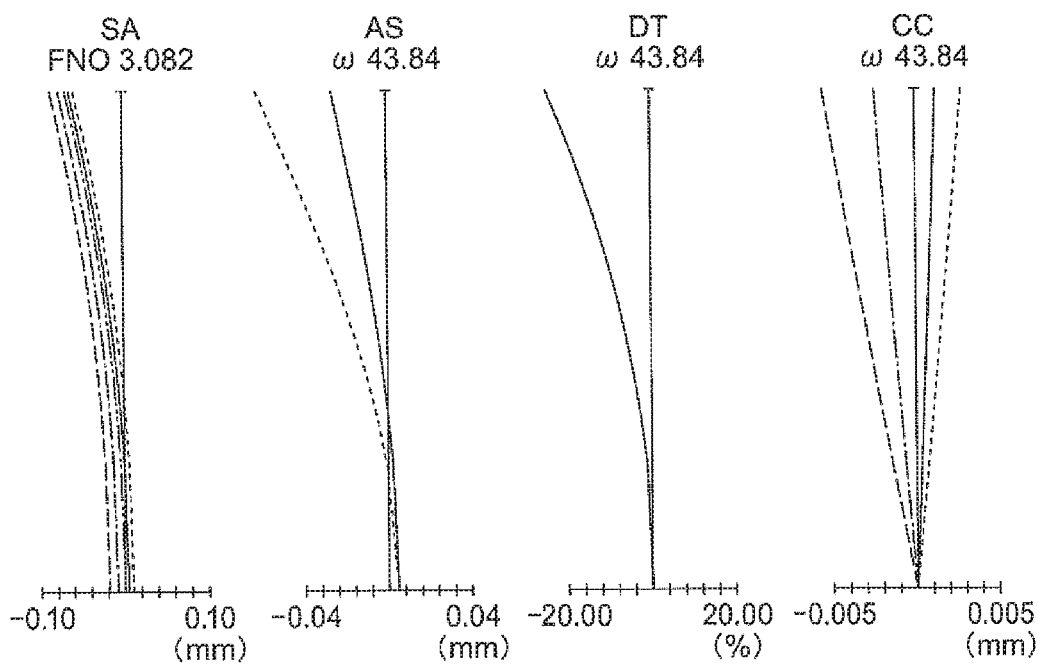

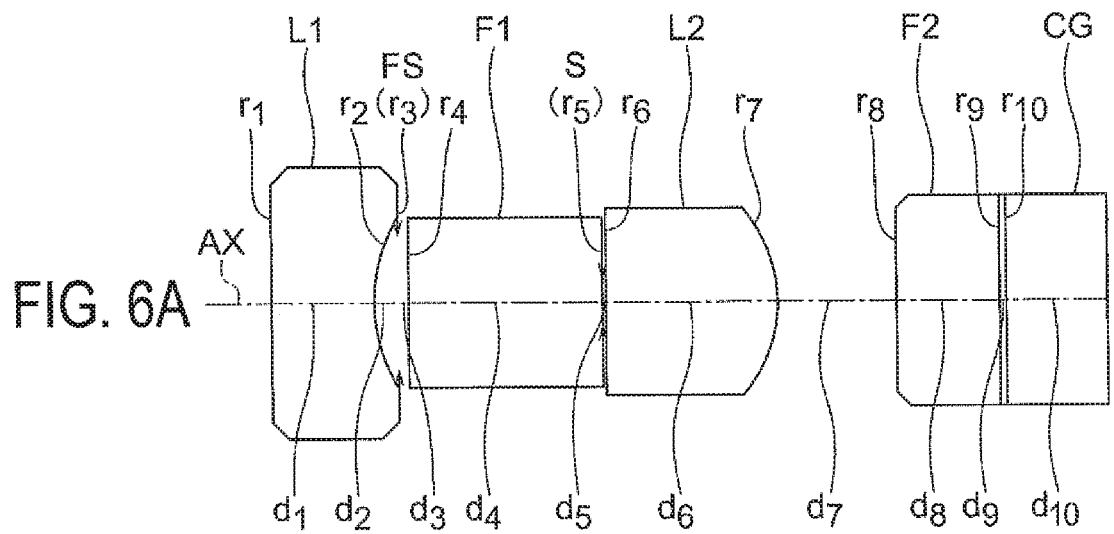
FIG. 6A
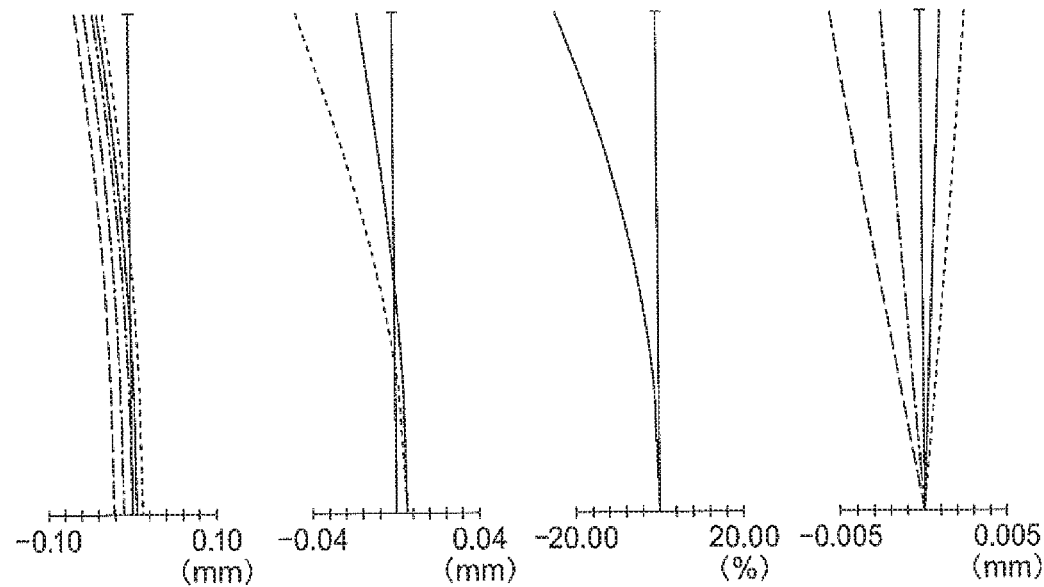

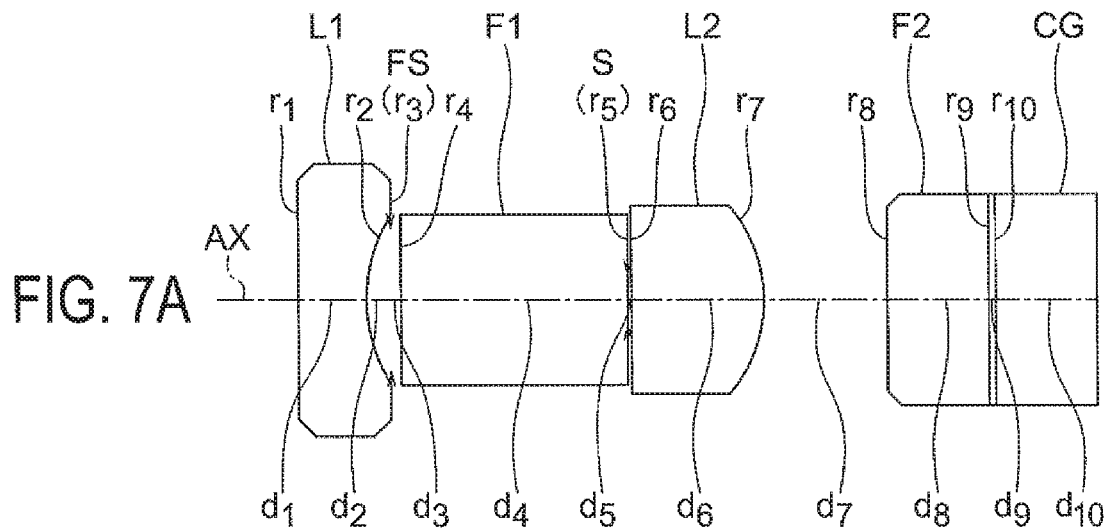
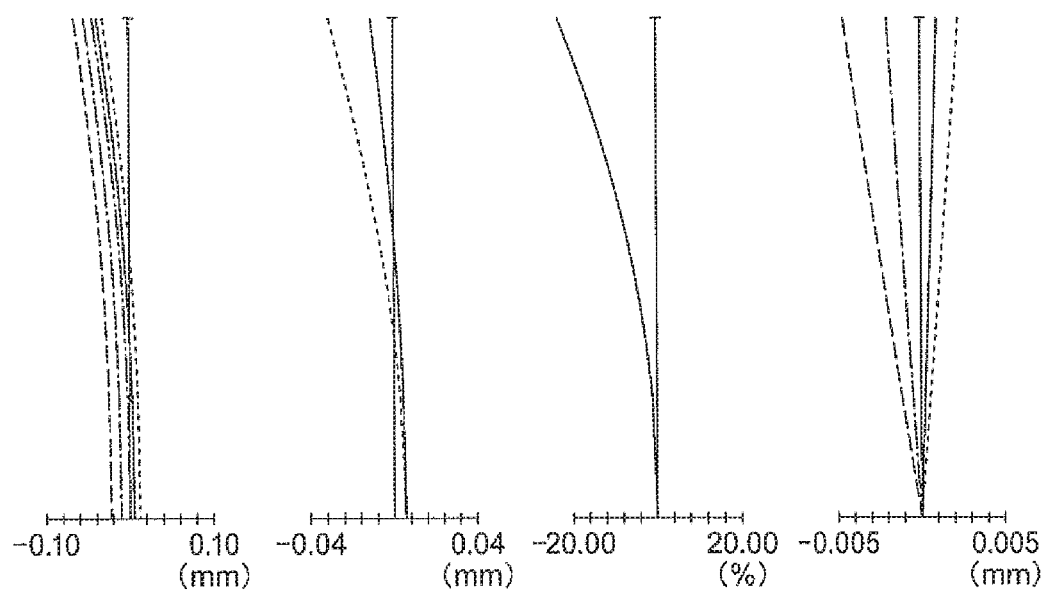

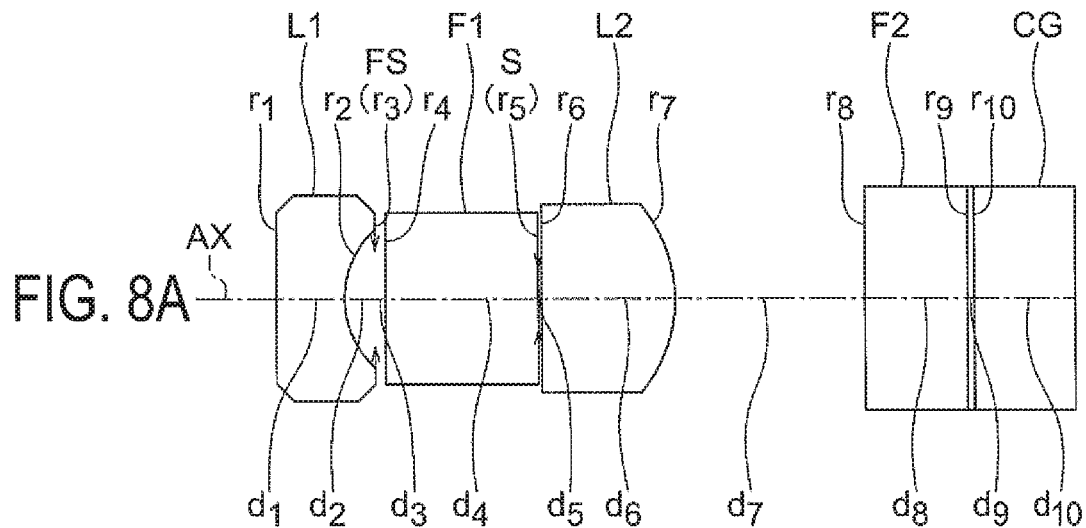
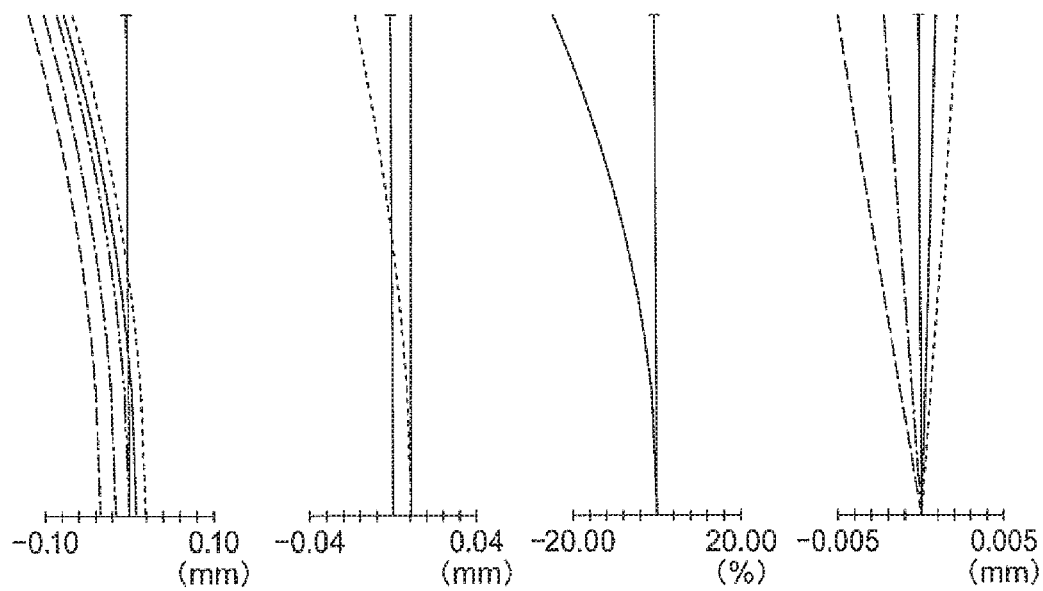

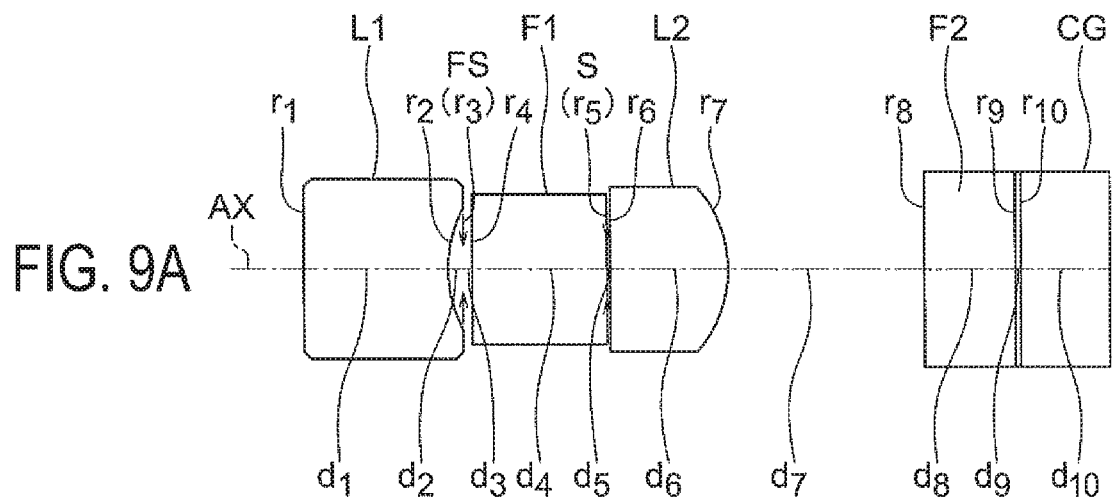
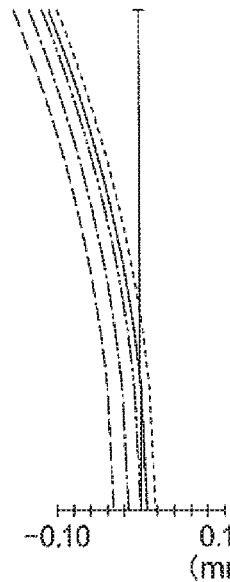
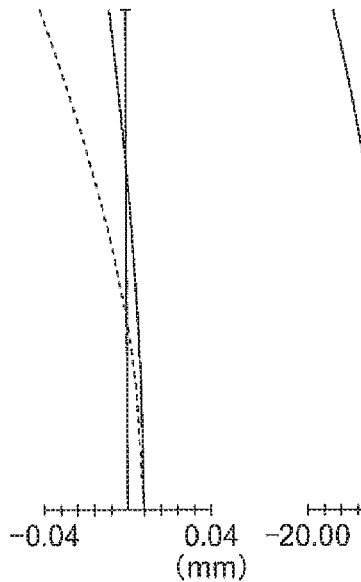
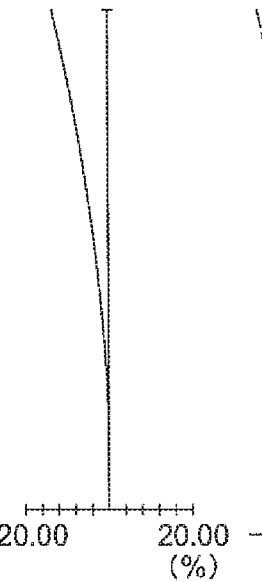
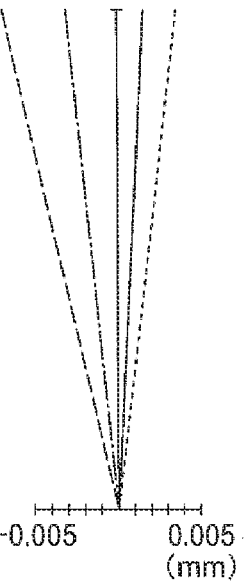

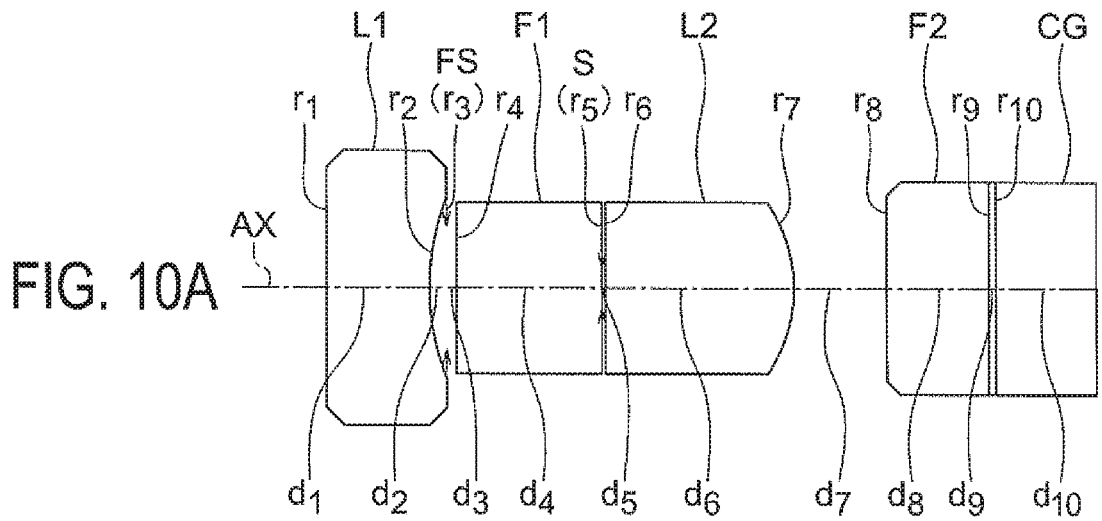
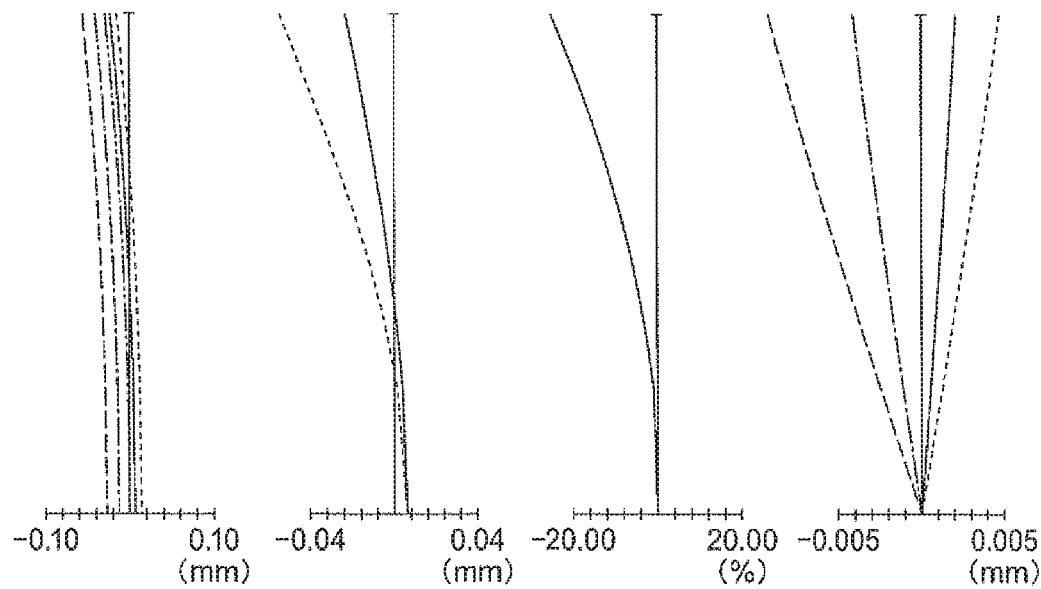

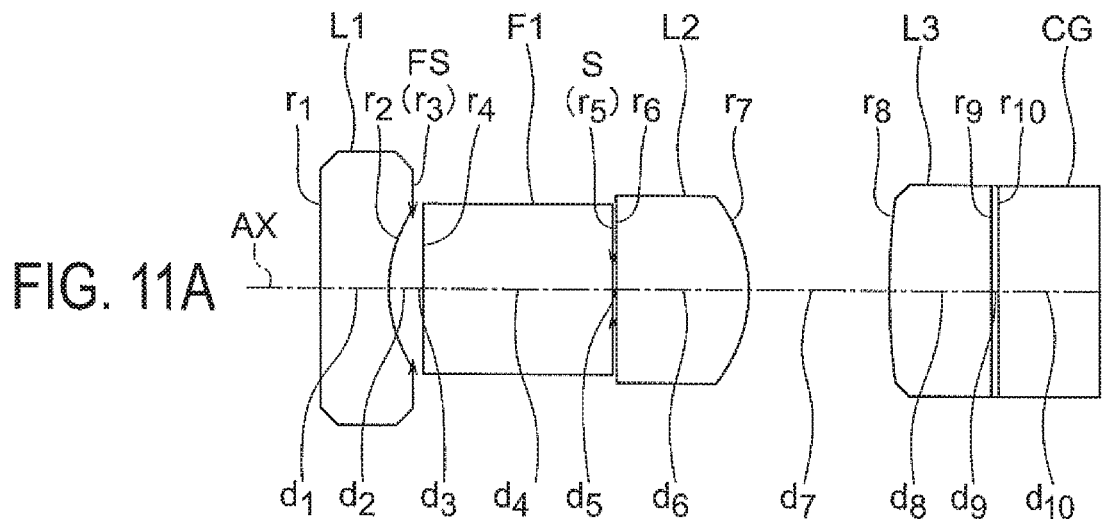
FIG. 11A
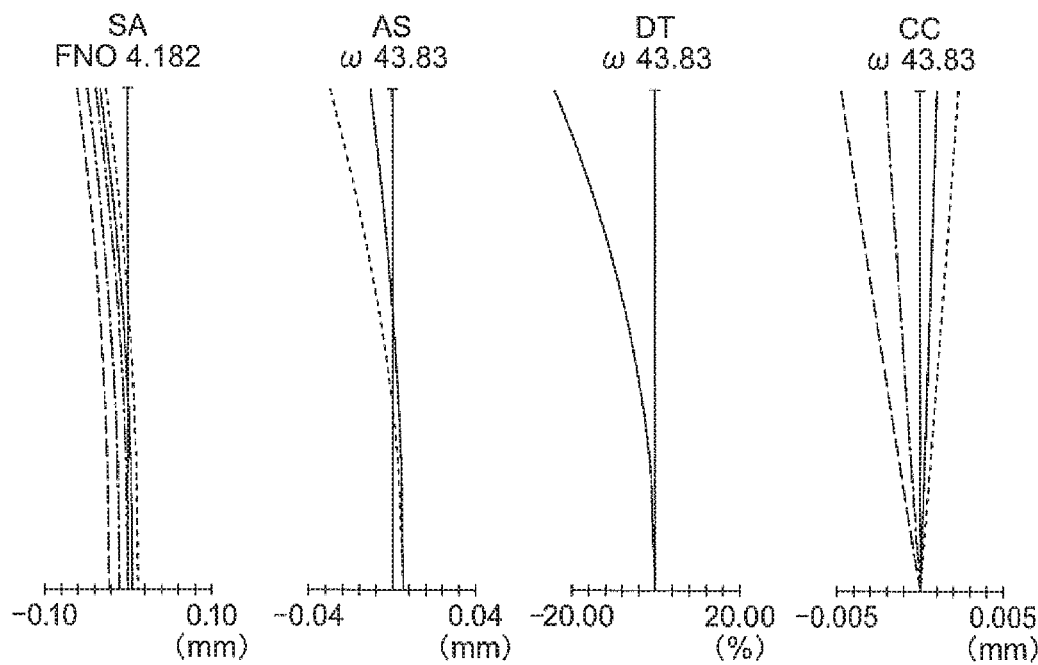
FIG. 11B
SA
FNO 4.182
FIG. 11C
AS
ω 43.83
FIG. 11D
DT
ω 43.83
FIG. 11E
CC
ω 43.83

ENDOSCOPE OBJECTIVE OPTICAL SYSTEM

CROSS-REFERENCE TO RELATED APPLICATION

The present application is a continuation application of PCT/JP2016/080773 filed on Oct. 18, 2016 which is based upon and claims the benefit of priority from Japanese Patent Application No. 2015-230522 filed on Nov. 26, 2015; the entire contents of which are incorporated herein by reference.

BACKGROUND OF THE INVENTION

Field of the Invention

The present invention relates to an endoscope objective optical system, and particularly to an electronic endoscope for a medical application, and more particularly to an endoscope objective optical system that is suitable for autoclave sterilization and a treatment using laser light.

Description of the Related Art

In an endoscope for a medical purpose, reducing the size of an inserting portion that is to be inserted into the body has heretofore been necessary for realizing minimally invasive diagnosis and treatment to reduce stress on a patient. To reduce the size of the inserting portion, reducing the size of an overall length and an outer diameter of a front-end optical system is indispensable. However, reducing the size of an optical system degrades the workability of an optical element, and assembly thereof also becomes difficult. As a result, productivity is degraded.

Moreover, in a reusable endoscope, cleansing and sterilization of the endoscope becomes significant. As a method of cleansing and sterilization, autoclave sterilization for example is a simple and effective sterilization method. Therefore, it is desirable that an endoscope to be reused is suitable for the autoclave sterilization.

In autoclave sterilization, an instrument is kept in a high-temperature and high-pressure water-vapor atmosphere, and bacteria adhered to the instrument are killed. With respect to optical elements of the endoscope, a coefficient of thermal expansion differs for a holding frame and a glass material. For such reason, in a case of carrying out the autoclave sterilization of the instrument, due to a change in temperature at the time of autoclave sterilization, the glass material may be subjected to a substantial stress, and be damaged. For this, it is desirable that the optical element has a durability to resist autoclave sterilization.

Furthermore, there are cases in which an endoscope is to be used for a treatment by laser light, such as a urinary-calculus treatment. In this case, when crushing light such as Nd—YAG laser (neodymium yttrium aluminum garnet, wavelength 1064 nm) to be irradiated to the urinary calculus is incident on an image pickup element, halation of an endoscope image occurs.

Moreover, for verifying an irradiation position of laser light for crushing, sometimes laser light of a wavelength of a visible-light region such as a wavelength close to an infra-red region is to be irradiated as laser light for target targeting. In this case, when the laser light for targeting is incident on an image pickup element, halation of an endoscope image occurs.

For preventing such halation of an endoscope image, it is effective to provide a cut filter having an adequate optical density to an optical system. For this, a filter that cuts laser light of a predetermined wavelength region, which is a cause of halation, is to be inserted into an optical path.

Here, cut filters are broadly divided into reflection-type cut filters and absorption-type cut filters. The reflection-type cut filter reflects light of a predetermined wavelength, and does not let to pass through. In a case of using the reflection-type cut filter, light reflected becomes a cause of halation which is optically undesirable.

Whereas, the absorption-type cut filter absorbs light of a predetermined band by a filter. Therefore, the absorption-type cut filter does not give rise to reflected light that is unnecessary. Consequently, for preventing halation, it is desirable to dispose an absorption-type cut filter having an adequate optical density in an optical path of the optical system.

For such reasons, it is desirable that an endoscope objective optical system has a mechanical durability at the time of autoclave sterilization, and includes an absorption-type cut filter having an adequate thickness for preventing halation due to laser light, thereby realizing a compact arrangement with favorable productivity.

Arrangements disclosed in Japanese Patent Application Laid-open Publication No. 2008-262193, Japanese Patent Application Laid-open Publication No. 2009-294494, and Japanese Patent Application Laid-open Publication No. 2009-288682 are examples of an arrangement of an endoscope objective optical system in which an optical element is reduced in size and a filter that cuts predetermined wavelength regions is disposed.

SUMMARY OF THE INVENTION

The present invention is an endoscope objective optical system that is to be combined with a solid image pickup element, comprising in order from an object side, a planoconcave negative lens, an absorption-type filter, an aperture stop, and a planoconvex positive lens, wherein the following conditional expressions (1), (2-1), (3-1), (4-1), and (4-2) are satisfied:

$$0.5 \leq tg1/tl \leq 0.8 \quad (1)$$

$$0.9 < |fn/ft| < 2.1 \quad (2\text{-}1),$$

$$0.15 \leq tIRCF/tl \quad (3\text{-}1),$$

$$1.2 < |fp/ft| < 1.7 \quad (4\text{-}1), \text{ and}$$

$$0.85 < |tp'/rp| < 1.3 \quad (4\text{-}2)$$

where, tg1 denotes a length along an optical axis from an object-side surface of the planoconcave negative lens up to an image-side surface of the planoconvex positive lens, tl denotes an overall length of the endoscope objective optical system, fn denotes a focal length of the planoconcave negative lens, ft denotes a focal length of the overall endoscope objective optical system, tIRCF denotes a thickness on the optical axis of the absorption-type filter, fp denotes a focal length of the planoconvex positive lens, tp' denotes a thickness on the optical axis of the planoconvex positive lens, and rp denotes a radius of curvature of a convex surface of the planoconvex positive lens.

BRIEF DESCRIPTION OF THE DRAWINGS

FIG. 2A is a cross-sectional view of an arrangement of an endoscope objective optical system according to an example 1, and FIG. 2B, FIG. 2C, FIG. 2D, and FIG. 2E are aberrations diagrams showing a spherical aberration (SA), an astigmatism (AS), a distortion (DT), and a chromatic aberration of magnification (CC) respectively;

FIG. 3A is a cross-sectional view of an arrangement of an endoscope objective optical system according to an example 2, and FIG. 3B, FIG. 3C, FIG. 3D, and FIG. 3E are aberration diagrams showing a spherical aberration (SA), an astigmatism (AS), a distortion (DT), and a chromatic aberration of magnification (CC) respectively;

FIG. 4A is a cross-sectional view of an arrangement of an endoscope objective optical system according to an example 3, and FIG. 4B, FIG. 4C, FIG. 4D, and FIG. 4E are aberration diagrams showing a spherical aberration (SA), an astigmatism (AS), a distortion (DT), and a chromatic aberration of magnification (CC) respectively;

FIG. 5A is a cross-sectional view of an arrangement of an endoscope objective optical system according to an example 4, and FIG. 5B, FIG. 5C, FIG. 5D, and FIG. 5E are aberration diagrams showing a spherical aberration (SA), an astigmatism (AS), a distortion (DT), and a chromatic aberration of magnification (CC) respectively;

FIG. 6A is a cross-sectional view of an arrangement of an endoscope objective optical system according to an example 5, and FIG. 6B, FIG. 6C, FIG. 6D, and FIG. 6E are aberration diagrams showing a spherical aberration (SA), an astigmatism (AS), a distortion (DT), and a chromatic aberration of magnification (CC) respectively;

FIG. 7A is a cross-sectional view of an arrangement of an endoscope objective optical system according to an example 6, and FIG. 7B, FIG. 7C, FIG. 7D, and FIG. 7E are aberration diagrams showing a spherical aberration (SA), an astigmatism (AS), a distortion (DT), and a chromatic aberration of magnification (CC) respectively;

FIG. 8A is a cross-sectional view of an arrangement of an endoscope objective optical system according to an example 7, and FIG. 8B, FIG. 8C, FIG. 8D, and FIG. 8E are aberration diagrams showing a spherical aberration (SA), an astigmatism (AS), a distortion (DT), and a chromatic aberration of magnification (CC) respectively;

FIG. 9A is a cross-sectional view of an arrangement of an endoscope objective optical system according to an example 8, and FIG. 9B, FIG. 9C, FIG. 9D, and FIG. 9E are aberration diagrams showing a spherical aberration (SA), an astigmatism (AS), a distortion (DT), and a chromatic aberration of magnification (CC) respectively;

FIG. 10A is a cross-sectional view of an arrangement of an endoscope objective optical system according to an example 9, and FIG. 10B, FIG. 10C, FIG. 10D, and FIG. 10E are aberration diagrams showing a spherical aberration (SA), an astigmatism (AS), a distortion (DT), and a chromatic aberration of magnification (CC) respectively;

FIG. 11A is a cross-sectional view of an arrangement of an endoscope objective optical system according to an example 10, and FIG. 11B, FIG. 11C, FIG. 11D, and FIG. 11E are aberration diagrams showing a spherical aberration (SA), an astigmatism (AS), a distortion (DT), and a chromatic aberration of magnification (CC) respectively.

DETAILED DESCRIPTION OF THE INVENTION

Embodiments of an endoscope objective optical system will be described below in detail by referring to the accompanying diagrams. However, the present invention is not restricted to the embodiments and the examples described below.

Figure 1:
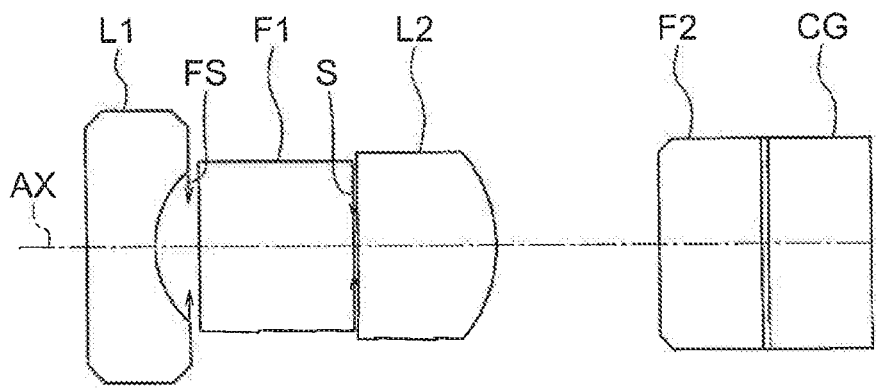
FIG. 1 is a cross-sectional view of an arrangement of an endoscope objective optical system according to an embodiment.

FIG. 1 is a cross-sectional view of a lens arrangement of an endoscope objective optical system according to an embodiment.

The present embodiment is an endoscope objective optical system that is to be combined with a solid image pickup element, which includes in order from an object side, a planoconcave negative lens L1 having a flat surface directed toward the object side, a flare aperture FS, an absorption-type filter (plane parallel plate) F1, an aperture stop S, and a planoconvex positive lens L2 having a flat surface directed toward the object side, wherein the following conditional expression (1) is satisfied:

$$0.5 \leq tg1/tl \leq 0.8 \quad (1)$$

where, tg1 denotes a length along an optical axis AX from an object-side surface of the planoconcave negative lens L1 up to an image-side surface of the planoconvex positive lens L2, and tl denotes an overall length of the endoscope objective optical system, or in other words, a length along the optical axis AX from the object-side surface of the planoconcave negative lens L1 up to an image-side surface of the planoconcave negative lens L1.

Parameter tg1 corresponds to a length of a portion including almost all lenses having a power. Conditional expression (1) regulates a proportion of parameter tg1 occupying the overall length.

By satisfying conditional expression (1), a back focus of the endoscope objective optical system becomes short, and shortening of the overall length is facilitated. Moreover, a thickness of each optical element becomes large, and processing, holding, and assembling of components become easy.

Moreover, the large thickness of the optical element also contributes to an improvement in durability of the optical element with respect to a thermal stress exerted from a holding frame at the time of autoclave sterilization.

Moreover, the large thickness of the absorption-type filter (plane parallel plate) F1 enables cutting laser light of a predetermined wavelength region by adequate absorption. Accordingly, it is possible to prevent halation of an endoscope image due to laser light for targeting, for example.

Furthermore, as mentioned above, when an endoscope is to be used for a treatment by laser light, such as the urinary-calculus treatment, laser light for crushing such as Nd—YAG is irradiated to a calculus. When such laser light is incident on an image pickup element, halation of an endoscope image occurs.

Therefore, it is desirable to apply a coating of a reflecting film that reflects Nd—YAG laser light, on at least one surface of the absorption-type filter F1.

In a case of exceeding an upper limit value of conditional expression (1), it is not possible to secure a back-focus length required for focus adjustment.

It is preferable that the following conditional expression (1') be satisfied instead of conditional expression (1).

$$0.5 \leq tg1/tl \leq 0.65 \quad (1')$$

In the endoscope objective optical system of the present embodiment, it is desirable that the absorption-type filter is an infra-red absorption filter.

For instance, sometimes, laser light of an infra-red region which is visible light, is to be used as the laser light for target. Accordingly, by cutting the laser light of the infra-red region, it is possible to reduce the halation of the endoscope image.

Moreover, in the endoscope objective optical system of the present embodiment, it is preferable that the following conditional expressions (2), (3), and (4) are satisfied:

$$0.32 \leq tn/\phi n \leq 1.4 \quad (2),$$

$$0.32 \leq tIRCF/\phi IRCF \leq 1.4 \quad (3), \text{ and}$$

$$0.32 \leq tp/\phi p \leq 1.4 \quad (4)$$

where, tn denotes a total thickness of the planoconcave negative lens L1,

φn denotes an outer diameter of the planoconcave negative lens L1, tIRCF denotes a thickness of the absorption-type filter (plane parallel plate) F, φIRCF denotes an outer diameter of the absorption-type filter (plane parallel plate) F, tp denotes a total thickness of the planoconvex positive lens L2, and φp denotes an outer diameter of the planoconvex positive lens L2.

The 'total thickness' refers to a thickness of an outer peripheral portion of the optical element. The 'thickness' refers to a thickness on an optical axis of the optical element.

Conditional expressions (2), (3), and (4) regulate a relationship of the outer diameter and the thickness of the planoconcave negative lens L1, the absorption-type filter (plane parallel plate) F1, and the planoconvex positive lens L2 respectively.

In a case of falling below lower limit values of conditional expressions (2), (3), and (4), processing and ease of assembly of the optical system is deteriorated, and resistance with respect to the autoclave sterilization is also degraded.

Moreover, in the case of falling below the lower limit values of conditional expressions (2), (3), and (4), the planoconcave negative lens L1, the absorption-type filter (plane parallel plate) F1, and the planoconvex positive lens L2 have tilting and decentering, and an astigmatism and a coma occur.

In a case of exceeding upper limit values of conditional expressions (2), (3), and (4), it results in the overall length of the optical system becoming long.

Moreover, in a reduced-size optical system, there is a clearance of about 4% of an outer diameter of an element between an optical element and a frame due to a manufacturing error. For an optical performance, it is desirable to suppress the tilting of the optical element in the lens frame due to the clearance, to be not more than 10°.

Figure 12:
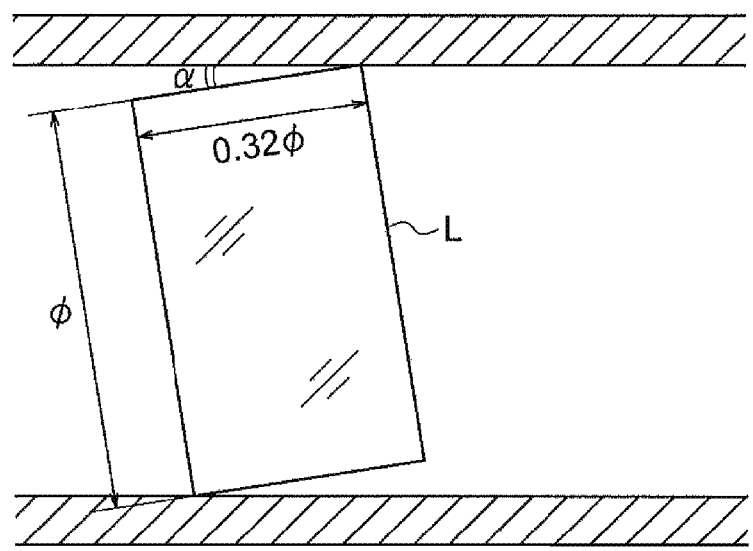
FIG. 12 is a diagram showing tilt of an optical element.

FIG. 12 is a diagram showing tilt of an optical element L in the form of a plane parallel plate having an outer diameter φ. For suppressing an angle α of tilt of the optical element L to be not more than 10°, a value of (a total thickness of the optical element L)/(the outer diameter φ of the optical element L) is required to be higher than 0.32.

By setting the value of (a thickness of the optical element L)/(the outer diameter φ of the optical element L), or in other words, the lower limit values of conditional expressions (2), (3), and (4), to be higher than 0.32, an adjustment of an angle of the optical element L becomes unnecessary, and ease of assembly is improved. Furthermore, when the thickness is made large with respect to the outer diameter of the optical element L, the durability with respect to stress from an outer peripheral portion exerted at the time of autoclave sterilization is also improved.

It is more preferable that the following conditional expressions (2'), (3'), and (4') be satisfied instead of conditional expressions (2), (3), and (4):

$$0.33 \leq tn/\phi n \leq 1.34 \quad (2'),$$

$$0.33 \leq tIRCF/\phi IRCF \leq 1.34 \quad (3'), \text{ and}$$

$$0.33 \leq tp/\phi p \leq 1.34 \quad (4')$$

Moreover, in the endoscope objective optical system of the present embodiment, it is desirable that the following conditional expressions (2-1), (3-1), (4-1), and (4-2) are satisfied:

$$0.9 < |fn/ft| < 2.1 \quad (2\text{-}1),$$

$$0.15 \leq tIRCF/tl \quad (3\text{-}1),$$

$$1.2 < |fp/ft| < 1.7 \quad (4\text{-}1), \text{ and}$$

$$0.85 < |tp'/rp| < 1.3 \quad (4\text{-}2)$$

where, fn denotes a focal length of the planoconcave negative lens, ft denotes a focal length of the overall endoscope objective optical system, tIRCF denotes the thickness of the absorption-type filter, tl denotes the overall length of the endoscope objective optical system, fp denotes a focal length of the planoconvex positive lens, tp' denotes a thickness of the planoconvex positive lens, and rp denotes a radius of curvature of a convex surface of the planoconvex positive lens.

Conditional expression (2-1) regulates a power distribution of the biconcave negative lens L1 and the overall endoscope objective optical system.

In a case of exceeding an upper limit value of conditional expression (2-1), a height of a light ray incident on a first surface on the object side of the biconcave negative lens L1 becomes high, and flare is generated.

In a case of falling below a lower limit value of conditional expression (2-1), a curvature of a concave surface of the planoconcave negative lens L1 becomes strong, and workability of the lens is deteriorated.

Conditional expression (3-1) regulates a relationship of the thickness of the absorption-type filter (plane parallel plate) F1 and the overall length. In the endoscope objective optical system having the abovementioned arrangement, by satisfying conditional expression (3-1), it is possible to secure an adequate thickness of the absorption-type filter. Consequently, it is possible to cut light of a wavelength region causing halation, and to prevent the halation.

Conditional expression (4-1) regulates a power distribution of the planoconvex positive lens L2 and the overall endoscope objective optical system.

In a case of falling below a lower limit value of conditional expression (4-1), it is not possible to secure the back-focus length required for the focus adjustment.

In a case of exceeding an upper limit value of conditional expression (4-1), the power of the planoconvex positive lens L2 is inadequate, and the overall length of the optical system becomes long.

Conditional expression (4-2) regulates a relationship of the thickness and the radius of curvature of the planoconvex positive lens L2. In a case of falling below a lower limit value of conditional expression (4-2) or in a case of exceeding an upper limit value of conditional expression (4-2), the centering workability of the lens is deteriorated.

EXAMPLE 1

An endoscope objective optical system according to an example 1 will be described below. FIG. 2A is a lens cross-sectional view of the endoscope objective optical system according to the present example.

In the present example, the endoscope objective optical system includes in order from an object side, a planoconcave negative lens L1, a flare aperture FS, a plane parallel plate F1, an aperture stop S, a planoconvex positive lens L2, a plane parallel plate F2, and a plane parallel plate CG.

The plane parallel plate F1 is an infra-red absorption filter. The plane parallel plate F2 and the plane parallel plate CG are cemented. Here, d9 is an adhesive layer.

FIG. 2B, FIG. 2C, FIG. 2D, and FIG. 2E show a spherical aberration (SA), an astigmatism (AS), a distortion (DT), and a chromatic aberration of magnification (CC) respectively, of the present example. The aberration diagrams are for each of wavelengths 656.27 nm (C-line), 587.56 nm (d-line), 540.07 (e-line), 486.13 nm (F-line), and 435.83 nm (g-line). Moreover, in each diagram, FNO denotes an F-number, and 'ω' denotes a half angle of view. The same is true for the other aberration diagrams described below.

EXAMPLE 2

An endoscope objective optical system according to an example 2 will be described below. FIG. 3A is a lens cross-sectional view of the endoscope objective optical system according to the present example.

In the present example, the endoscope objective optical system includes in order from an object side, a planoconcave negative lens L1, a flare aperture FS, a plane parallel plate F1, an aperture stop S, a planoconvex positive lens L2, a planoconvex positive lens L3, and a plane parallel plate CG.

The plane parallel plate F1 is an infra-red absorption filter. The planoconvex positive lens L3 is a field lens. The planoconvex positive lens L3 and the plane parallel plate CG are cemented. Here, d9 is an adhesive layer.

FIG. 3B, FIG. 3C, FIG. 3D, and FIG. 3E show a spherical aberration (SA), an astigmatism (AS), a distortion (DT), and a chromatic aberration of magnification (CC) respectively, of the present example.

EXAMPLE 3

An endoscope objective optical system according to an example 3 will be described below. FIG. 4A is a lens cross-sectional view of the endoscope objective optical system according to the present example.

In the present example, the endoscope objective optical system includes in order from an object side, a planoconcave negative lens L1, a flare aperture FS, a plane parallel plate F1, an aperture stop S, a planoconvex positive lens L2, a planoconvex positive lens L3, and a plane parallel plate CG.

The plane parallel plate F1 is an infra-red absorption filter. The planoconvex positive lens L3 is a field lens. The planoconvex positive lens L3 and the plane parallel plate CG are cemented. Here, d9 is an adhesive layer.

FIG. 4B, FIG. 4C, FIG. 4D, and FIG. 4E show a spherical aberration (SA), an astigmatism (AS), a distortion (DT), and a chromatic aberration of magnification (CC) respectively, of the present example.

EXAMPLE 4

An endoscope objective optical system according to an example 4 will be described below. FIG. 5A is a lens cross-sectional view of the endoscope objective optical system according to the present example.

In the present example, the endoscope objective optical system includes in order from an object side, a planoconcave negative lens L1, a flare aperture FS, a plane parallel plate F1, an aperture stop S, a planoconvex positive lens L2, a plane parallel plate F2, and a plane parallel plate CG.

The plane parallel plate F1 is an infra-red absorption filter. The plane parallel plate F2 and the plane parallel plate CG are cemented. Here, d9 is an adhesive layer.

FIG. 5B, FIG. 5C, FIG. 5D, and FIG. 5E show a spherical aberration (SA), an astigmatism (AS), a distortion (DT), and a chromatic aberration of magnification (CC) respectively, of the present example.

EXAMPLE 5

An endoscope objective optical system according to an example 5 will be described below. FIG. 6A is a lens cross-sectional view of the endoscope objective optical system according to the present example.

In the present example, the endoscope objective optical system includes in order from an object side, a planoconcave negative lens L1, a flare aperture FS, a plane parallel plate F1, an aperture stop S, a planoconvex positive lens L2, a plane parallel plate 2, and a plane parallel plate CG.

The plane parallel plate F1 is an infra-red absorption filter. The plane parallel plate F2 and the plane parallel plate CG are cemented. Here, d9 is an adhesive layer.

FIG. 6B, FIG. 6C, FIG. 6D, and FIG. 6E show a spherical aberration (SA), an astigmatism (AS), a distortion (DT), and a chromatic aberration of magnification (CC) respectively, of the present example.

EXAMPLE 6

An endoscope objective optical system according to an example 6 will be described below. FIG. 7A is a lens cross-sectional view of the endoscope objective optical system according to the present example.

In the present example, the endoscope objective optical system includes in order from an object side, a planoconcave negative lens L1, a flare aperture FS, a plane parallel plate F1, an aperture stop S, a planoconvex positive lens L2, a plane parallel plate F2, and a plane parallel plate CG.

The plane parallel plate F1 is an infra-red absorption filter. The plane parallel plate F2 and the plane parallel plate CG are cemented. Here, d9 is an adhesive layer.

FIG. 7B, FIG. 7C, FIG. 7D, and FIG. 7E show a spherical aberration (SA), an astigmatism (AS), a distortion (DT), and a chromatic aberration of magnification (CC) respectively, of the present example.

EXAMPLE 7

An endoscope objective optical system according to an example 7 will be described below. FIG. 8A is a lens cross-sectional view of the endoscope objective optical system according to the present example.

In the present example, the endoscope objective optical system includes in order from an object side, a planoconcave negative lens L1, a flare aperture FS, a plane parallel plate F1, an aperture stop S, a planoconvex positive lens L2, a plane parallel plate F2, and a plane parallel plate CG.

The plane parallel plate F1 is an infra-red absorption filter. The plane parallel plate F2 and the plane parallel plate CG are cemented. Here, d9 is an adhesive layer.

FIG. 8B, FIG. 8C, FIG. 8D, and FIG. 8E show a spherical aberration (SA), an astigmatism (AS), a distortion (DT), and a chromatic aberration of magnification (CC) respectively, of the present example.

EXAMPLE 8

An endoscope objective optical system according to an example 8 will be described below. FIG. 9A is lens cross-sectional view of the endoscope objective optical system according to the present example.

In the present example, the endoscope objective optical system includes in order from an object side, a planoconcave negative lens L1, a flare aperture FS, a plane parallel plate F1, an aperture stop S, a planoconvex positive lens L2, a plane parallel plate F2, and a plane parallel plate CG.

The plane parallel plate F1 is an infra-red absorption filter. The plane parallel plate F2 and the plane parallel plate CG are cemented. Here, d9 is an adhesive layer.

FIG. 9B, FIG. 9C, FIG. 9D, and FIG. 9E show a spherical aberration (SA), an astigmatism (AS), a distortion (DT), and a chromatic aberration of magnification (CC) respectively, of the present example.

EXAMPLE 9

An endoscope objective optical system according to an example 9 will be described below. FIG. 10A is a lens cross-sectional view of the endoscope objective optical system according to the present example.

In the present example, the endoscope objective optical system includes in order from an object side, a planoconcave negative lens L1, a flare aperture FS, a plane parallel plate F1, an aperture stop S, a planoconvex positive lens L2, a plane parallel plate F2, and a plane parallel plate CG.

The plane parallel plate F1 is an infra-red absorption filter. The plane parallel plate F2 and the plane parallel plate CG are cemented. Here, d9 is an adhesive layer.

FIG. 10B, FIG. 10C, FIG. 10D, and FIG. 10E show a spherical aberration (SA), an astigmatism (AS), a distortion (DT), and a chromatic aberration of magnification (CC) respectively, of the present example.

EXAMPLE 10

An endoscope objective optical system according to an example 10 will be described below. FIG. 11A is a lens cross-sectional view of the endoscope objective optical system according to the present example.

In the present example, the endoscope objective optical system includes in order from an object side, a planoconcave negative lens L1, a flare aperture FS, a plane parallel plate F1, an aperture stop S, a planoconvex positive lens L2, a planoconvex positive lens L3, and a plane parallel plate CG.

The plane parallel plate F1 is an infra-red absorption filter. The planoconvex positive lens L3 is a field lens. The planoconvex positive lens L3 and the plane parallel plate CG are cemented. Here, d9 is an adhesive layer.

FIG. 11B, FIG. 11C, FIG. 11D, and FIG. 11E show a spherical aberration (SA), an astigmatism (AS), a distortion (DT), and a chromatic aberration of magnification (CC) respectively, of the present example.

Numerical data of each example described above is shown below. In Surface data, r denotes radius of curvature of each lens surface, d denotes a distance between respective lens surfaces, ne denotes a refractive index of each lens for a e-line, vd denotes an Abbe number for each lens, Fno denotes an F number, and IH denotes an image height. Moreover, ER denotes an effective diameter, FS denotes a flare aperture, and S denotes an aperture stop. Here, T650 is an internal transmittance of the absorption-type filter at 650 nm.

EXAMPLE 1

Unit mm

Surface data

| Surface no. | r | d | ne | vd | ER |
|---|---|---|---|---|---|
| 1 | ∞ | 0.200 | 1.77066 | 71.79 | 0.80 |
| 2 | 0.300 | 0.100 | | | |
| 3 (FS) | ∞ | 0.030 | | | 0.30 |
| 4 | ∞ | 0.450 | 1.52300 | 65.13 | 0.50 |
| 5 (S) | ∞ | 0.010 | | | 0.17 |
| 6 | ∞ | 0.410 | 1.88815 | 40.76 | 0.55 |
| 7 | −0.427 | 0.474 | | | |
| 8 | ∞ | 0.300 | 1.51825 | 64.14 | 0.62 |
| 9 | ∞ | 0.020 | 1.50688 | 64.00 | 0.62 |
| 10 | ∞ | 0.300 | 1.61350 | 50.49 | 0.62 |
| Image plane | ∞ | | | | |

Various data

| | |
|---|---|
| Focal length (mm) | 0.334 |
| Angle of view (°) | 90.6 |
| Fno | 4.186 |
| $T_{650}$ (%) | 12.28 |
| tl (mm) | 2.29 |

EXAMPLE 2

Unit mm

Surface data

| Surface no. | r | d | ne | vd | ER |
|---|---|---|---|---|---|
| 1 | ∞ | 0.200 | 1.77066 | 71.79 | 0.80 |
| 2 | 0.300 | 0.090 | | | |
| 3 (FS) | ∞ | 0.030 | | | 0.30 |
| 4 | ∞ | 0.450 | 1.52300 | 65.13 | 0.50 |
| 5 (S) | ∞ | 0.010 | | | 0.16 |
| 6 | ∞ | 0.390 | 1.88815 | 40.76 | 0.55 |
| 7 | −0.459 | 0.520 | | | |
| 8 | 0.951 | 0.340 | 1.51825 | 64.14 | 0.65 |
| 9 | ∞ | 0.020 | 1.50688 | 64.00 | 0.65 |
| 10 | ∞ | 0.300 | 1.61350 | 50.49 | 0.65 |
| Image plane | ∞ | | | | |

-continued

Unit mm

Various data

| | |
|---|---|
| Focal length (mm) | 0.310 |
| Angle of view (°) | 96.9 |
| Fno | 4.079 |
| $T_{650}$ (%) | 12.28 |
| tl (mm) | 2.35 |

EXAMPLE 3

Unit mm

Surface data

| Surface no. | r | d | ne | vd | ER |
|---|---|---|---|---|---|
| 1 | ∞ | 0.210 | 1.77066 | 71.79 | 0.80 |
| 2 | 0.408 | 0.050 | | | |
| 3 (FS) | ∞ | 0.030 | | | 0.32 |
| 4 | ∞ | 0.360 | 1.52300 | 65.13 | 0.80 |
| 5 (S) | ∞ | 0.010 | | | 0.13 |
| 6 | ∞ | 0.350 | 1.88815 | 40.76 | 0.60 |
| 7 | −0.374 | 0.300 | | | |
| 8 | 2.963 | 0.300 | 1.51825 | 64.14 | 0.62 |
| 9 | ∞ | 0.020 | 1.50688 | 64.00 | 0.62 |
| 10 | ∞ | 0.300 | 1.61350 | 50.49 | 0.62 |
| Image plane | ∞ | | | | |

Various data

| | |
|---|---|
| Focal length (mm) | 0.336 |
| Angle of view (°) | 87.5 |
| Fno | 4.182 |
| $T_{650}$ (%) | 18.67 |
| tl (mm) | 1.93 |

EXAMPLE 4

Unit mm

Surface data

| Surface no. | r | d | ne | vd | ER |
|---|---|---|---|---|---|
| 1 | ∞ | 0.300 | 1.77066 | 71.79 | 0.80 |
| 2 | 0.540 | 0.050 | | | |
| 3 (FS) | ∞ | 0.030 | | | 0.36 |
| 4 | ∞ | 0.450 | 1.52300 | 65.13 | 0.50 |
| 5 (S) | ∞ | 0.010 | | | 0.17 |
| 6 | ∞ | 0.500 | 1.88815 | 40.76 | 0.55 |
| 7 | −0.390 | 0.271 | | | |
| 8 | ∞ | 0.300 | 1.51825 | 64.14 | 0.62 |
| 9 | ∞ | 0.020 | 1.50688 | 64.00 | 0.62 |
| 10 | ∞ | 0.300 | 1.61350 | 50.49 | 0.62 |
| Image plane | ∞ | | | | |

Various data

| | |
|---|---|
| Focal length (mm) | 0.337 |
| Angle of view (°) | 87.7 |
| Fno | 3.082 |
| $T_{650}$ (%) | 12.28 |
| tl (mm) | 2.23 |

EXAMPLE 5

Unit mm

Surface data

| Surface no. | r | d | ne | vd | ER |
|---|---|---|---|---|---|
| 1 | ∞ | 0.300 | 1.77066 | 71.79 | 0.80 |
| 2 | 0.492 | 0.070 | | | |
| 3 (FS) | ∞ | 0.030 | | | 0.40 |
| 4 | ∞ | 0.570 | 1.52300 | 65.13 | 0.50 |
| 5 (S) | ∞ | 0.010 | | | 0.14 |
| 6 | ∞ | 0.500 | 1.88815 | 40.76 | 0.55 |
| 7 | −0.424 | 0.346 | | | |
| 8 | ∞ | 0.300 | 1.51825 | 64.14 | 0.62 |
| 9 | ∞ | 0.020 | 1.50688 | 64.00 | 0.62 |
| 10 | ∞ | 0.300 | 1.61350 | 50.49 | 0.62 |
| Image plane | ∞ | | | | |

Various data

| | |
|---|---|
| Focal length (mm) | 0.335 |
| Angle of view (°) | 87.7 |
| Fno | 4.214 |
| $T_{650}$ (%) | 7.02 |
| tl (mm) | 2.45 |

EXAMPLE 6

Unit mm

Surface data

| Surface no. | r | d | ne | vd | ER |
|---|---|---|---|---|---|
| 1 | ∞ | 0.200 | 1.77066 | 71.79 | 0.80 |
| 2 | 0.476 | 0.070 | | | |
| 3 (FS) | ∞ | 0.030 | | | 0.42 |
| 4 | ∞ | 0.670 | 1.52300 | 65.13 | 0.50 |
| 5 (S) | ∞ | 0.010 | | | 0.15 |
| 6 | ∞ | 0.390 | 1.88815 | 40.76 | 0.55 |
| 7 | −0.428 | 0.361 | | | |
| 8 | ∞ | 0.300 | 1.51825 | 64.14 | 0.62 |
| 9 | ∞ | 0.020 | 1.50688 | 64.00 | 0.62 |
| 10 | ∞ | 0.300 | 1.61350 | 50.49 | 0.62 |
| Image plane | ∞ | | | | |

Various data

| | |
|---|---|
| Focal length (mm) | 0.334 |
| Angle of view (°) | 87.2 |
| Fno | 4.213 |
| $T_{650}$ (%) | 4.40 |
| tl (mm) | 2.35 |

EXAMPLE 7

Unit mm

Surface data

| Surface no. | r | d | ne | vd | ER |
|---|---|---|---|---|---|
| 1 | ∞ | 0.200 | 1.77066 | 71.79 | 0.60 |
| 2 | 0.270 | 0.090 | | | |
| 3 (FS) | ∞ | 0.030 | | | 0.28 |
| 4 | ∞ | 0.450 | 1.52300 | 65.13 | 0.50 |
| 5 (S) | ∞ | 0.010 | | | 0.18 |
| 6 | ∞ | 0.390 | 1.88815 | 40.76 | 0.55 |

-continued

| Unit mm | | | | | |
|---|---|---|---|---|---|
| 7 | −0.425 | 0.554 | | | |
| 8 | ∞ | 0.300 | 1.51825 | 64.14 | 0.65 |
| 9 | ∞ | 0.020 | 1.50688 | 64.00 | 0.65 |
| 10 | ∞ | 0.300 | 1.61350 | 50.49 | 0.65 |
| Image plane | ∞ | | | | |

| Various data | |
|---|---|
| Focal length (mm) | 0.333 |
| Angle of view (°) | 87.7 |
| Fno | 4.133 |
| $T_{650}$ (%) | 12.28 |
| tl (mm) | 2.34 |

EXAMPLE 8

| Unit mm | | | | | |
|---|---|---|---|---|---|
| Surface data | | | | | |
| Surface no. | r | d | ne | vd | ER |
| 1 | ∞ | 0.480 | 2.01169 | 28.27 | 0.60 |
| 2 | 0.44 | 0.050 | | | |
| 3 (FS) | ∞ | 0.030 | | | 0.24 |
| 4 | ∞ | 0.450 | 1.52300 | 65.13 | 0.50 |
| 5 (S) | ∞ | 0.010 | | | 0.20 |
| 6 | ∞ | 0.390 | 1.80922 | 39.59 | 0.55 |
| 7 | −0.416 | 0.650 | | | |
| 8 | ∞ | 0.300 | 1.51825 | 64.14 | 0.65 |
| 9 | ∞ | 0.020 | 1.50688 | 64.00 | 0.65 |
| 10 | ∞ | 0.300 | 1.61350 | 50.49 | 0.65 |
| Image plane | ∞ | | | | |

| Various data | |
|---|---|
| Focal length (mm) | 0.428 |
| Angle of view (°) | 66.0 |
| Fno | 4.063 |
| $T_{650}$ (%) | 12.28 |
| tl (mm) | 2.68 |

EXAMPLE 9

| Unit mm | | | | | |
|---|---|---|---|---|---|
| Surface data | | | | | |
| Surface no. | r | d | ne | vd | ER |
| 1 | ∞ | 0.300 | 2.01169 | 28.27 | 0.80 |
| 2 | 0.718 | 0.050 | | | |
| 3 (FS) | ∞ | 0.030 | | | 0.36 |
| 4 | ∞ | 0.430 | 1.52300 | 65.13 | 0.50 |
| 5 (S) | ∞ | 0.010 | | | 0.12 |
| 6 | ∞ | 0.550 | 2.01169 | 28.27 | 0.50 |
| 7 | −0.446 | 0.273 | | | |
| 8 | ∞ | 0.300 | 1.51825 | 64.14 | 0.62 |
| 9 | ∞ | 0.020 | 1.50688 | 64.00 | 0.62 |
| 10 | ∞ | 0.300 | 1.61350 | 50.49 | 0.62 |
| Image plane | ∞ | | | | |

| Various data | |
|---|---|
| Focal length (mm) | 0.342 |
| Angle of view (°) | 87.5 |
| Fno | 4.349 |
| $T_{650}$ (%) | 13.48 |
| tl (mm) | 2.26 |

EXAMPLE 10

| Unit mm | | | | | |
|---|---|---|---|---|---|
| Surface data | | | | | |
| Surface no. | r | d | ne | vd | ER |
| 1 | ∞ | 0.200 | 1.77066 | 71.79 | 0.80 |
| 2 | 0.420 | 0.070 | | | |
| 3 (FS) | ∞ | 0.030 | | | 0.42 |
| 4 | ∞ | 0.560 | 1.52300 | 65.13 | 0.50 |
| 5 (S) | ∞ | 0.010 | | | 0.15 |
| 6 | ∞ | 0.390 | 1.88815 | 40.76 | 0.55 |
| 7 | −0.440 | 0.410 | | | |
| 8 | 2.100 | 0.300 | 1.51825 | 64.14 | 0.62 |
| 9 | ∞ | 0.020 | 1.50688 | 64.00 | 0.62 |
| 10 | ∞ | 0.300 | 1.61350 | 50.49 | 0.62 |
| Image plane | ∞ | | | | |

| Various data | |
|---|---|
| Focal length (mm) | 0.333 |
| Angle of view (°) | 87.7 |
| Fno | 4.182 |
| $T_{650}$ (%) | 7.35 |
| tl (mm) | 2.29 |

Values of conditional expressions in each example are given below.

| Conditional expression | Example 1 | Example 2 | Example 3 | Example 4 |
|---|---|---|---|---|
| (1) tg1/tl | 0.52 | 0.50 | 0.52 | 0.60 |
| (2) tn/φn | 0.38 | 0.36 | 0.33 | 0.44 |
| (3) tIRCF/φIRCF | 0.90 | 0.90 | 0.45 | 0.90 |
| (4) tp/φp | 0.56 | 0.54 | 0.33 | 0.70 |
| (2-1) |fn/ft| | 1.17 | 1.26 | 1.58 | 2.08 |
| (3-1) tIRCF/tl | 0.20 | 0.19 | 0.19 | 0.20 |
| (4-1) |fp/ft| | 1.44 | 1.67 | 1.25 | 1.30 |
| (4-2) |tp'/rp| | 0.96 | 0.85 | 0.94 | 1.28 |

| Conditional expression | Example 5 | Example 6 | Example 7 |
|---|---|---|---|
| (1) tg1/tl | 0.61 | 0.58 | 0.50 |
| (2) tn/φn | 0.46 | 0.53 | 0.53 |
| (3) tIRCF/φIRCF | 1.14 | 1.34 | 0.90 |
| (4) tp/φp | 0.72 | 0.71 | 0.71 |
| (2-1) |fn/ft| | 1.91 | 1.85 | 1.05 |
| (3-1) tIRCF/tl | 0.23 | 0.28 | 0.19 |
| (4-1) |fp/ft| | 1.43 | 1.44 | 1.44 |
| (4-2) |tp'/rp| | 1.18 | 0.91 | 0.92 |

| Conditional expression | Example 8 | Example 9 | Example 10 |
|---|---|---|---|
| (1) tg1/tl | 0.53 | 0.61 | 0.55 |
| (2) tn/φn | 0.52 | 0.95 | 0.53 |
| (3) tIRCF/φIRCF | 0.90 | 0.86 | 1.12 |
| (4) tp/φp | 0.71 | 1.10 | 0.71 |

-continued

| Conditional expression | Example 8 | Example 9 | Example 10 |
|---|---|---|---|
| (2-1) \|fn/ft\| | 1.02 | 2.07 | 1.63 |
| (3-1) tIRCF/tl | 0.17 | 0.19 | 0.24 |
| (4-1) \|fp/ft\| | 1.20 | 1.29 | 1.49 |
| (4-2) \|tp'/rp\| | 0.94 | 1.23 | 0.89 |

The present embodiment shows an effect that it is possible to provide an endoscope objective optical system resistant to a temperature change at the time of autoclave sterilization, which prevents the halation due to laser light, and in which an overall length of the optical system is short and the processing and assembling of lenses is easy.

The embodiment and various examples of the present invention are described above. However, the present invention is not restricted to these embodiment and examples, and embodiments formed by combining arrangement of these embodiment and examples without departing from the scope of the present invention are also included in the category of the present invention.

Thus, the present invention is useful for an endoscope objective optical system resistant to a temperature change at the time of autoclave sterilization, which prevents the halation due to laser light, and in which an overall length of the optical system is short and the processing and assembling of lenses is easy.

What is claimed is:

1. An endoscope objective optical system that is to be combined with a solid image sensor, the endoscope optical system comprising in order from an object side:
a planoconcave negative lens;
an absorption-type filter;
an aperture stop; and
a planoconvex positive lens,
wherein the following conditional expressions (1), (2-1), (3-1'), (4-1), and (4-2) are satisfied:

$$0.5 \leq tg1/tl \leq 0.8 \quad (1),$$

$$0.9 < |fn/ft| < 2.1 \quad (2\text{-}1),$$

$$0.15 \leq tIRCF/tl \leq 0.28 \quad (3\text{-}1'),$$

$$1.2 < |fp/ft| < 1.7 \quad (4\text{-}1), \text{ and}$$

$$0.85 < |tp'/rp| < 1.3 \quad (4\text{-}1),$$

where:
tg1 denotes a length along an optical axis from an object-side surface of the planoconcave negative lens up to an image-side surface of the planoconvex positive lens,
tl denotes an overall length of the endoscope objective optical system,
fn denotes a focal length of the planoconcave negative lens,
ft denotes a focal length of the overall endoscope objective optical system,
tIRCF denotes a thickness on the optical axis of the absorption-type filter,
fp denotes a focal length of the planoconvex positive lens,
tp' denotes a thickness on the optical axis of the planoconvex positive lens, and
rp denotes a radius of curvature of a convex surface of the planoconvex positive lens.

2. The endoscope objective optical system according to claim 1, wherein the absorption-type filter is an infra-red absorption filter.

3. An endoscope comprising:
the endoscope objective optical system according to claim 1.

* * * * *